United States Patent
Reetz et al.

(10) Patent No.: US 9,428,771 B2
(45) Date of Patent: Aug. 30, 2016

(54) METHOD FOR THE OXIDATION OF ORGANIC COMPOUNDS

(75) Inventors: Manfred T. Reetz, Marburg (DE); Felipe Emilio Zilly Claude, Köln (DE)

(73) Assignee: STUDIENGESELLSCHAFT KOHLE MBH, Muelheim an der Ruhr (DE)

( * ) Notice: Subject to any disclaimer, the term of this patent is extended or adjusted under 35 U.S.C. 154(b) by 425 days.

(21) Appl. No.: 13/824,056

(22) PCT Filed: Sep. 6, 2011

(86) PCT No.: PCT/DE2011/075211
§ 371 (c)(1),
(2), (4) Date: Apr. 30, 2013

(87) PCT Pub. No.: WO2012/062299
PCT Pub. Date: May 18, 2012

(65) Prior Publication Data
US 2013/0236940 A1    Sep. 12, 2013

(30) Foreign Application Priority Data
Sep. 17, 2010   (DE) .................. 10 2010 045 662

(51) Int. Cl.
C12P 7/16     (2006.01)
C12N 9/02     (2006.01)
C12P 7/02     (2006.01)

(52) U.S. Cl.
CPC ............... *C12P 7/16* (2013.01); *C12N 9/0071* (2013.01); *C12P 7/02* (2013.01); *Y02P 20/52* (2015.11)

(58) Field of Classification Search
None
See application file for complete search history.

(56) References Cited

PUBLICATIONS

Pons, Nicoletta, et al; "Interaction of polyhalogenated compounds of appropriate configuration with mammalian or bacterial CYP enzymes increased bilirubin and uroporphyrinogen oxidation in vitro"; Biochemical Pharmacology 66 (2003) pp. 405-414.
Zilly, Felipe, E. et al; "Tuning a P450 enzyme for methane oxidation"; Agnew. Chem. Int. Ed. (2011) 50, pp. 2720-2724.
Meinhold, Peter, et al; "Direct conversion of ethane to ethanol by engineered cytochrome P450 BM3"; ChemBioChem (2005), 6, pp. 1765-1768.
Fasan, Rudi et al; "Engineered alkane-hydroxylating cytochrome P450 BM3 exhibiting nativelike catalytic properties"; Agnew. Chem. Int. Ed. (2007), 46, pp. 8414-8418.

*Primary Examiner* — Thane Underdahl
*Assistant Examiner* — Aaron J Kosar
(74) *Attorney, Agent, or Firm* — Norris McLaughlin & Marcus, P.A.

(57) ABSTRACT

A method is described for the oxidation of organic compounds in which the organic compound that is to be oxidized is brought to reaction in an aqueous solution in the presence of cytochrome P 450, and wherein perfluorinated organic compound is added to the aqueous reaction mixture as activator.

14 Claims, No Drawings

METHOD FOR THE OXIDATION OF ORGANIC COMPOUNDS

This application is a 371 of PCT/DE2011/075211, filed Sep. 6, 2011, which claims foreign priority benefit under 35 U.S.C. §119 of the German Patent Application No. 10 2010 045 662.4 filed Sep. 17, 2010, the disclosures of which are incorporated herein by reference.

The present invention relates to a method for raising the activity and increasing the regio- and stereoselectivity of cytochrome P450 enzymes as catalysts for the oxidation of organic compounds.

Cytochrome P450 enzymes (CYPs) are heme-dependent monooxygenases which are capable of catalyzing in particular C—H activating oxidations of organic compounds by introducing alcohol functions (C—H→C—OH) but also epoxidations of olefins (P. R. Ortiz de Montellano, Cytochrome P450: Structure, Mechanism and Biochemistry, 3rd Edition, Springer, 2005; E. M. Isin, F. P. Guengerich, Biochim. Biophys. Acta 2007, 1770, 314-329). In nature, they occur in many organisms, particularly as catalysts in the biosynthesis of various natural substances and in detoxification processes. They are specifically used in biotechnology to catalyze certain oxidative transformations under mild conditions, in which atmospheric oxygen (or hydrogen peroxide) functions as oxidant, frequently by using whole cells from a host organism such as *E. coli* or yeast cells (V. B. Urlacher, S. Eiben, Trends in Biotechnology 2006, 24, 324-330; R. Bernhardt, J. Biotechnol. 2006, 124, 128-145).

Unfortunately these biotechnological methods have narrow limits, since many substrates of industrial interest are only slowly converted by CYPs or are not accepted at all, while in other cases inadequate regioselectivity and/or low stereoselectivity is observed (K. Drauz, H. Waldmann, Enzyme Catalysis in Organic Synthesis: A Comprehensive handbook, Vol I-III, Wiley-VCH, Weinheim, 3rd Edition, 2002). The binding sites of CYPs are generally known to be very large, which hinders a specific or optimal binding of the substrate to be oxidized at the catalytically active Fe-heme center or even renders it highly unlikely (P. R. Ortiz de Montellano, Cytochrome P450: Structure, Mechanism and Biochemistry, 3rd Edition, Springer, 2005). The mechanism of action of CYP has been intensively studied, and thus it is known, for example, that rapidly reacting substrates are initially bound to the binding site, a process which induces activation of the CYP, since water is displaced from the Fe-heme center by transition from the low-spin state to the catalytically active high-spin state (P. R. de Montellano, Cytochrome P450: Structure, Mechanism and Biochemistry, 3rd Edition, Springer, 2005; A. W. Andrews, H. M. Girvan, K. J. McLean, Nat. Prod. Rep. 2007, 24, 585-609).

In order to solve the problems of the lack of, or inadequate, activity and also poor regio- and stereoselectivity, protein engineering has been applied in some cases, either in the form of site-directed mutagenesis or of directed evolution (S. Kumar, "Engineering cytochrome P450 biocatalysts for biotechnology, medicine and bioremediation", Expert Opinion in Drug Metab. Toxicol. 2009, 6, 1-17; R. D. Schmid, et al, J. Biotechnol. 2001, 88, 167-171; A. Glieder, E. T. Farinas, F. H. Arnold, Nature Biotechnol 2002, 20, 1135-1139; M. W. Peteers, P. Meinwald, A. Glieder, F. H. Arnold, J. Am. Chem. Soc. 2003, 125, 13442-13450; E. M. J. Gillam, Chem. Res. Toxicol. 2008, 21, 220-231). These molecular biological methods are, however, not only complex and expensive, where such a method generally takes months, they are by no means routinely successful. Examples include the P450-BM3-catalyzed hydroxylation of small alkanes such as propane, ethane and methane. Despite extensive efforts to apply directed evolution to this CYP, it has not been successful to date to evolve sufficiently high activities for practical application to the oxidation of ethane or propane, while methane could not be reacted at all (P. Meinwald, M. W. Peters, M. M. Y. Chen, K. Takahashi, F. H. Arnold, ChemBioChem 2005, 6, 1765-1768; S. Kumar, Expert Opinion in Drug Metab. Toxicol. 2009; 6, 1-17). The optimal steric binding of a substrate directly to the catalytically active Fe-heme center is, however, also critical for the regio- and stereoselective oxidation of all substrates, even of relatively large compounds, such as for the oxidative hydroxylation of terpenes, steroids and synthetic organic compounds. Selective C—H activation poses a major challenge. A simple, practical and economical method is desired that allows the activity and optionally also the regio- and stereoselectivity of CYP-catalysed oxidation processes to be controlled or improved, particularly as the products are of great industrial interest. Examples are the production of methanol from methane and isopropanol from propane and also the regio- and stereoselective hydroxylation of precursor compounds with formation of intermediates for medicaments.

The present invention relates to a surprisingly simple method for improving the activity, regioselectivity and/or stereoselectivity of CYPs, without having to use molecular biology-supported mutagenesis. According to the invention, a perfluorinated organic compound, here referred to as additive, is added to a CYP, whereby the catalytic profile is improved by enhancing the substrate acceptance and increasing the activity and also, in relevant cases, by raising the regio- and/or stereoselectivity. After addition of the additive, it binds spontaneously in the binding site of the enzyme, whereby the catalytic profile is positively influenced without the additive itself being oxidized. Perfluorinated organic compounds are generally known to be chemically inert, since perfluorinated radicals of such molecules do not undergo any reactions under normal conditions (D. M. Lemal, J. Org. Chem. 2004, 69, 1-11). For this reason, perfluorinated organic compounds are suitable as additives in the method according to the invention. They are not themselves oxidized by the CYP; however, they influence the effective size of the respective binding site and affect the required catalytic activation and also increase the regio- and stereoselectivity.

In the simplest case, perfluorinated alkanes according to the invention serve as additive:

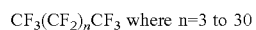

$CF_3(CF_2)_nCF_3$ where n=3 to 30

In particular, perfluorinated organic compounds according to the invention have at least one functional group (e.g. —OH, —$CO_2H$, —$SO_3H$, —$PO_3H$ and also salts thereof having counterions of the type $Li^-$, $Na^+$, $K^+$, $Cs^+$, $Mg^{2+}$, $Zn^{+2}$, $H_4N^-$, $(CH_3)_4N^-$, $(C_4H_9)_4N^+$. The organic scaffold may be aliphatic, olefinic or aromatic, or combinations thereof. Also suitable for the invention are, for example, perfluorinated primary alcohols $CF_3(CF_2)_nOH$ with n=0 to 30 such as perfluorinated n-octanol, secondary or tertiary analogues thereof, and also perfluorinated phenols such as pentafluorophenol.

Preference is given, but by no means exclusively, to perfluorinated aliphatic carboxylic acids. The term "perfluorinated carboxylic acid" is understood by those skilled in the art to mean the perfluorinated analogues of carboxylic acids $RCO_2H$ or dicarboxylic acids $HO_2C$—(R)—$CO_2H$, in which the C—H bonds have been replaced by C—F bonds and the R-radical is an aliphatic or aromatic carbon skeleton with corresponding C—F bonds. The various perfluorinated carboxylic acids or salts thereof may be used according to the invention during the catalytic oxidation processes, in which both aliphatic and aromatic perfluorinated carboxylic acids are useful, including chiral perfluorinated carboxylic acids, such as 9-Me-undecanoic acid and 8-Et-undecanoic acid. An example of a perfluorinated aromatic carboxylic acid is pentafluorobenzoic acid. Preference is given to perfluorinated carboxylic acids of type (I) or salts thereof (II).

$CF_3(CF_2)_nCO_2H$ where n=0 to 30, and
$CF_3(CF_2)_nCO_2^-M^+$ where n=0 to 30 and $M^+$=a metal cation such as $Li^+$, $Na^+$, $K^+$, $Mg^{2+}$, $Zn^{2+}$ or an ammonium cation such as $NH_4^+$ or $(n-butyl)_4N^+$.

According to the invention, one or more C—H units of a substrate to be oxidized, which is not an additive in terms of the invention as stated above, is converted to the respective alcohol function (C—H→C—OH), or an olefin function is converted to the corresponding epoxide. Examples of substrates to be oxidized are straight-chain or branched alkanes or alkenes having 1 to 30, particularly 1 to 12 carbon atoms.

Two reaction procedures are possible according to the invention: 1. The use in vitro of the corresponding enzymes, or 2. the use of whole cells.

According to the invention, an organic solvent is also added to the aqueous reaction solution, in addition to the activating additive, to render the substrate to be oxidized more soluble. Examples include ethanol, isopropanol, dimethylformamide, acetonitrile and tetrahydrofuran.

All CYPs are useful according to the invention as biocatalyst. To those skilled in the art the CYPs can be found in the corresponding data banks, for example on Dr. David Nelson's website (www.drnelson.uthsc.edu/cytochromeP450), and the following data banks www.p450.riceblast.snu.ac.kr (CYPs from the kingdom of fungi), bank on protein engineering of CYPs) give information on all the CYPs which can be used according to the invention. Particularly advantageous are the so-called fusion CYPs, such as P450 BM3 (A. W. Munro et al., Trends in Biochemical Sciences, 2002, 27, 250-257), in which FAD/FMN- and NADPH-cytochrome P450 reductase, in various binding domains, are fused in a polypeptide (V. B. Urlacher, S. Eiben, Trends in Biotechnology, 2006, 24, 324-330; P. R. de Montellano, Cytochrome P450: Structure, Mechanism and Biochemistry, $3^{rd}$ edition, Springer, 2005).

CYPs occur in the kingdom of animals, plants and microorganisms. The family of the CYPs is usually divided into four classes. The first class comprises CYPs which accept electrons from a specific ferredoxin (an iron-sulfur (2Fe-2S)-protein), which transfers electrons from an NAD(P)H-dependent ferredoxin reductase to CYP. Mitochondrial and the majority of bacterial CYPs, such as P450cam from *Pseudomonas putida*, belong to this class.

CYPs belonging to the second class receive electrons directly from an NADPH-cytochrome P450 reductase (CPR). This reductase consists of an FAD domain and an FMN domain. The majority of microsomal CYPs belong to this class, are membrane bound and receive electrons from a universal CPR. To the second class of CYPs also belong the CYPs combining both functional units—a CYP domain (also known as heme domain) and a reductase domain—in a single polypeptide chain. These enzymes are characterized by their high catalytic rates, since the electron transfer from the reductase to the heme domain is efficiently coupled, and is not limited by the diffusion rates of the individual components. Particular representatives of this class include the CYPs 102A, in particular the bacterial CYPs 102A1-CYPA12, with very particular emphasis on CYP 102A1 from *Bacillus megaterium*, P450-BM3.

The CYPs belonging to the third class do not require any cofactors as electron donors, since they can be oxidized directly by means of an $H_2O_2$ substrate. A representative of this class is $P450_{BS}$ from *Bacillus subtilis*.

CYPs from class four can accept electrons directly from NADH and do not require any further domains or reductases.

In addition, there are CYP representatives which cannot be clearly assigned to the first or second class. These are mainly fusion proteins in which the CYP/heme domain has been fused with at least one other domain.

A representative of this group is CYP116 (PFOR=P450-phthalate dioxygenase reductase), in which an FMN domain and a ferredoxin domain have been fused to the CYP domain. A second example is CYP51FX ex M. capsulatus (McCYP51FX), which has a CYP domain and a ferredoxin domain. CYP177A1 (XplA), which has an FMN and a CYP domain, is found in *A. thaliana*. As a final example, CYP221A1 ex *P. fluorescens* (ACAD-P450=putative P450-acyl CoA dehydrogenase fusion) shall be mentioned, which has an FAD and a CYP domain.

In one aspect, the invention relates to a method in which additives are added to a crude CYP enzyme lysate. In a further aspect of the invention, the additive is added to purified CYP. In another aspect the invention relates to a method in which the additive is added to whole cells which express CYP. In one embodiment the latter refers to an endogenously expressed CYP. In another embodiment the cells express recombinant CYP. A particular embodiment comprises the use of whole cells expressing recombinant CYP and expressing no endogenous CYP or in which endogenous CYP has been switched off by genetic manipulation or in which the endogenous CYP expression has been suppressed by a chemical substance. The methods can be designed such that whole cells are used which express the CYP on the extracellular side of the cell membrane. Alternatively the CYPs are secreted following the expression. In further embodiments the CYP is expressed intracellularly and co-solvents, cyclodextrines, detergents, substances forming pores in the cell membrane are mixed into the reaction mixture, in addition to the additive. A further object of the invention are methods in which the additives are added to cells expressing CYP and additional proteins such as shuttle, transporter, antiporter, symporter and channels, which increase the transport of the additive into the cell.

For the recombinant expression, mammalian CYPs can be expressed, for example, in bacterial cells or yeast cells. It is also feasible to express bacterial CYPs in foreign bacterial cells, mammalian cells or yeast cells. Yeast CYPs can be expressed in either foreign yeast cells, bacterial cells or mammalian cells. The same also applies to the expression of plant CYPs. It is sufficiently known to those skilled in the art which gene technology provisions need to be taken in this respect.

Preferred CYPs are: CYP102, CYP1A1, CYP1A2, CYP2A6, CYP1B1, CYP2B1, CYP2B4, CYP2B6, CYP2C8, CYP2C9, CYP2C18, CYP2C19, CYP2D6, CYP2E1, CYP3A4, CYP3A5, CYP101A1, CYP106A2 and CYP154.

In one aspect, the invention refers to human CYPs, particularly to CYPs of the CYP1, CYP2, CYP3 and CYP4 classes. Examples here include, without restriction: CYP1 family: CYP1A1; CYP1A2; CYP1B1; CYP2 family: CYP2A6; CYP2A13; CYP2B6; CYP2C8; CYP2C9; CYP2C19; CYP2D6; CYP2E1; CYP2F1; CYP2J2;

CYP2R1; CYP2S1; CYP2W1; CYP3 family: CYP3A4; CYP3A5; CYP3A7; CYP3A43; CYP4 family: CYP4A11; CYP4A22; CYP4B1; CYP4F2. Particularly emphasized also are the following human CYPs: CYP5A1; CYP8A1; CYP11A1, CYP11B1, CYP11B2, CYP19A1; CYP21A2; CYP26A1.

The abovementioned CYPs can originate from another mammal instead of human. Preferred organisms from which these CYPs are derived are: rat, mouse, cow and pig.

Particular preference is given to the bacterial CYPs of the CYPs 102 class, e.g. CYP102A1, CYP102A2, CYP102A3, CYP102A4, CYP102A5, CYP102A6, CYP102A7, CYP102A8, CYP102A9, CYP102A10, CYP102A11, CYP102A12. Very particularly preferred candidates of this class can be taken from Table 1.

TABLE 1

Preferred members of the CYP102A family

| CYP102 | Source |
|---|---|
| A1 | Bacillus megaterium DSMZ 32 |
| A2 | Bacillus subtilis |
| A3 | Bacillus subtilis |
| A4 | Bacillus anthracis str. Ames |
| A5 | Bacillus cereus ATCC 14579 |
| A6 | Bradyrhizobium japonicum USDA 110 |
| A7 | Bacillus licheniformis ATCC 14580 |
| A8 | Bacillus thuringiensis serovar konkukian str. 97-27 |
| A9 | Bacillus weihenstephanensis KBAB4 |
| A10 | Erythrobacter litoralis HTCC2594 |
| A11 | Erythrobacter sp. NAP1 |
| A12 | Rhodopseudomonas palustris HaA2 |

The claimed methods relate also to the use of mutants or chimera of the CYPs described above.

The selection of the oxidizing agent is not limited, according to the invention, to any defined oxidizing agent and all oxidizing agents may be used which do not negatively influence the reaction. Preferred oxidizing agents used are atmospheric oxygen, $H_2O_2$, cumene hydroperoxide, tert-butyl hydroperoxide, linoleic acid hydroperoxide, $NaClO_2$ and/or $NaIO_4$.

EXAMPLE 1

Preparation of a CYP Expression Vector

In general, advice for those skilled in the art on cloning of genes and for cultivating bacteria is found in Sambrook, Molecular Cloning, 2001, and in Current Protocols in Molecular Biology, Current Protocols in Microbiology and Current Protocols in Cell Biology, all from 2010. The gene p450-bm3/cyp102a1, which codes for the wildtype enzyme P450-BM3 from Bacillus megaterium (ATTC 14581, Strain No., 32 from DSMZ GmbH), was amplified from the genomic DNA by PCR and, by means of the enzyme restriction sites Nco I and Sac I, was cloned in the E. coli expression vector pETM11 (EMBL, Germany), such that the vector pETM11-P450-BM3-WT was obtained. 5' from the inserted DNA sequence, the vector pETM11 bears a nucleotide sequence which codes for six histidine amino acids. The protein resulting from the expression therefore bears an N-terminal polyhistidine tag. Furthermore, the vector is not provided with a kanamycin resistance cassette for selection purposes. The cloned gene expression is controlled by a T7/lac promoter.

EXAMPLE 2

Expression of a Recombinant CYP

E. coli BL21 (DE3) GOLD (Novagen) cells, which comprise a tetracycline resistance gene, were transformed with the pETM11-P450-BM3-WT vector by means of heat shock or electroporation. An aliquot of an overnight culture in LB medium, treated with kanamycin (20 mg/l) and tetracycline (12.5 mg/l) for selection purposes, was used to inoculate TB culture medium, which had been treated with 50 mg/l kanamycin, 0.1 g/l glutamate, 0.4% (v/v) glycerol, trace metals (50 µM $FeCl_3$, 20 µM $CaCl_2$, 10 µM $MnCl_2$, 10 µM $ZnSO_4$, 2 µM $CoCl_2$, 2 µM $CuCl_2$, 2 µM $NiCl_2$, 2 µM $Na_2MoO_4$, 2 µM $H_3BO_3$) and 1 mM $MgCl_2$. After culturing at 37° C. with horizontal shaking at 250 rpm and reaching an $OD_{600}$ of ~0.6-0.8, IPTG was added to give a final concentration of 100 µM, the temperature was reduced to 25° C. and the shaking rate was reduced from 250 rpm to 130 rpm. The expression was carried out for 24 hours. Subsequently the bacteria were harvested by centrifugation. The pellet was stored at −80° C. for further use.

EXAMPLE 3

Purification of a Recombinant CYP

For the digestion of the bacterial cells, the pellet was thawed and resuspended by addition of lysis buffer (25 mM Tris, 20% glycerol, 0.1% Tween-20 and 20 mg/l DNAse I (Applichem, Germany)). The cells were solubilized in the suspension by means of French press (American Instruments Company, Silverspring, USA) at a pressure of 1200 psi. The lysate obtained was centrifuged for 1 hour at 18000 g and 4° C. Subsequently the supernatant was filtered with a filter (0.22 µm).

The lysate was desalted using HiTrap desalting columns (bed volumes of 5 ml, GE Healthcare) and 100 mM Tris/HCl pH 7.8 buffer. This and the following chromatographic steps were carried out using ÄKTA purifier (GE Healthcare). The protein fractions were concentrated and subjected to anion exchange chromatography. This step was carried out in a similar manner to a protocol previously described (Schwaneberg U. et al., J. Chromat. A, 1999), in which Tosoh DEAE-5PW resin (Tosoh Bioscience, Japan) was used as stationary phase, which had been equilibrated with 100 mM Tris-HCl pH 7.8 buffer. The protein was eluted with a step gradient using 1 M NaCl, 100 mM Tris-HCl pH 7.8 buffer. The red-coloured, enzyme-containing fractions were combined. In total, approximately 0.8 µmol of purified wildtype P450 BM3 was obtained from 1 l of bacterial culture.

Determination of the Enzyme Concentration

The enzyme concentration was determined by means of a CO difference spectrum analysis (Omura T and Sato R, J Biol. Chem., 1964). For this purpose, the enzyme was diluted in a solution of 2% $Na_2S_2O_4$ in 100 mM KPi pH 8.0. The diluted solution was halved and distributed equally into 2 cuvettes. CO gas was passed through one of the two cuvettes for 30 seconds, the solution CO-saturated and the cuvette subsequently sealed with parafilm. After 5 minutes a difference spectrum was recorded using the two cuvettes. For this purpose, a 2401-PC spectrometer from Shimadzu was used. The difference spectrum was recorded from 350-500 nm and the difference in the absorption $A_{450\ nm}$-$A_{490\ nm}$ determined. The concentration of the enzyme solution was calculated using the millimolar extinction coefficients 91 determined by Omura and Sato (JBC, 1964).

EXAMPLE 4

Additives

The fluorinated additives used come from the following suppliers: perfluoroheptanoic acid (Aldrich), perfluorononanoic acid (ABCR), perfluorodecanoic acid (Aldrich), perfluoroundecanoic acid (ABCR), perfluorododecanoic acid (Acros), perfluorotridecanoic acid (Aldrich), perfluorotetradecanoic acid (Aldrich), perfluorohexadecanoic acid (ABCR), 6-(perfluoroethyl)hexanol (Fluorochem, GB), 1H, 1H, 1H, 2H, 2H, 3H, 3H-perfluoroundecanol (ABCR), 1H, 1H, 2H, 2H-perfluorooctan-1-ol (Fluorochem, GB).

The basic suitability of the additives can be tested by difference spectroscopy as follows. The binding of the additive to the active site of the enzyme is critical.

A dilution of the enzyme is prepared, e.g. 0.1-1 µM in 100 mM KPi pH 8.0. The diluted sample is divided equally into two quartz cuvettes. To one dilution is admixed the additive, while to the other is added the solvent, which was used for the additive, in the same ratio, to serve as a control sample. Typically, the additive is started at a concentration of approx. 10-100 µM; depending on the additive this can be increased, for example, up to 20 mM. After 5 minutes, the difference spectrum is recorded. For this purpose, a spectrometer, e.g. the 2401-PC spectrometer from Shimadzu, is used. The difference spectrum is recorded from 350-500 nm. Without additive on the heme, the enzyme shows no change in the difference spectrum. Suitable additives displace the water molecule co-ordinated to the heme in the enzyme resting state and bring about a change in spin state of the heme iron atom from low-spin to high-spin. This change in spin state can be observed in the difference spectrum by a fall in the absorption at approx. 417 nm and an increase at approx. 390 nm. This change in spin state means that the enzyme is now in a condition ready for the catalysis. The additive thus activates the enzyme. In other cases the additives are suitable if they generate the changes in the difference spectrum already described in the additional presence of the substrate (in both cuvettes). This means that when the additive thus positions the substrate in the enzyme binding site, the substrate displaces the water molecule. As further suitability checks, particularly for the initially mentioned additives, titration experiments with CYP enzyme inhibitors may be conducted. CYP inhibitors are mainly nitrogen-containing substances, which bind to the heme iron atom via the nitrogen, displace the water molecule, and through the binding to the iron atom, block the iron atom in the low spin state and inactivate the enzyme. In the difference spectrum, the binding of the inhibitors can be observed by an increase in the absorption at approx. 430-440 nm. Typical inhibitors are, for example, imidazole or n-octylamine. The suitable additives displace the inhibitor, such that in the difference spectrum a decrease at 430-440 nm and an increase at 390 nm can be observed. This additionally confirms that the additives actually bind to the active site of the enzyme.

EXAMPLE 5

Whole-Cell Catalysis

Various protocols may be carried out for whole-cell catalysis (Current Protocols in Cell Biology, Current Protocols in Microbiology). One of these stipulates that an *E. coli* culture of CYP-expressing cells is centrifuged for 10 min at 900 g and 4° C. and the pelleted cells are resuspended in 100 mM KPi, 5% glycerol (v/v) pH 7.4 and are centrifuged again under the same conditions. Thereupon the pellet is resuspended in 100 mM KPi, 5% glycerol (v/v), 5% glucose (w/v), 5 mM EDTA, 0.25 mM $NADP^+$, 1 U/ml GDH, antibiotics if required, pH 7.4. The cells are then shock-frozen and may be cryopreserved. The subsequently thawed cells are ready for catalysis. For this, the cell suspension, the substrate and the additive are mixed.

EXAMPLE 6

Oxidation of Alkanes (>$C_4$)

For hydroxylating alkanes, for example $C_6$ and $C_8$ alkanes, the substrate was added to the reaction solution from a 160 mM stock in EtOH and was adjusted to a final concentration of 3.2 mM. The solution further comprised 0.1 M glucose (Riedel de Haen), 1 mM $NADP^+$ (Codexis, Jülich, Germany), 1 U/ml GDH (#001, Codexis, Jülich, Germany), 1 mM additive (unless otherwise stated), BM3-WT enzyme and 100 mM KPi, pH 8.0 with a total volume of 20 ml. The reactions were shaken for 1 hour at 20° C. in a 50 ml Falcon reaction tube in a bacterial incubator at 130 rpm. After one hour, three aliquots were removed, each of 1 ml volume, and acidified with 0.1 ml of 10% HCl. Subsequently 1 mM 1-pentanol was added as internal standard. The mixture was extracted with half a volume of MTBE and analyzed by gas chromatography.

EXAMPLE 7

Gas Chromatographic Analysis of $C_6$ and $C_8$ Hydroxylation Products

Hydroxylation products were analyzed by GC using the following instruments and under the following conditions: HP6890+7683HP (Hewlett Packard, USA); column: 15 m Stabilwax phase, internal diameter 0.25 mm, film thickness 0.5 µm, (J&W, Germany); pressure: 0.8 bar H2; split rate 60; injector: 220° C.; temperature gradient: 40° C. 4 min isotherm, 40-60° C. at 4° C./min, 60° C.-250° C. at 15° C./min. FID detector. The product peaks were quantified as a ratio to the 1 mM 1-pentanol peak using the following, previously determined, correction factors: 2-octanol: 2.36; 3-,4-octanol: 2.23; 2-,3-hexanol:1.218; 3-Me-3-PeOH,3-Me-2-PeOH: 1.49; 3,3-Di-Me-2-BuOH: 1.43; 2,3-Di-Me-BuOH: 1.317.

The following substrates, for example, were analyzed:
Additive: $CF_3(CF_2)_nCO_2H$
1a: n=0; 1b: n=5; 1c: n=7; 1d: n=8; 1e: n=9; 1f: n=10; 1g: n=11; 1h: n=12

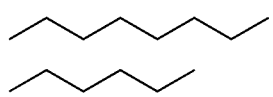

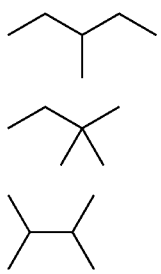

Table 2|P450-BM3 catalysed oxidation of alkanes in the presence and absence of perfluorocarboxylic acids 1. Reaction conditions: 3.2 mM alkane; 1% v/v DMF; 2% v/v ethanol; 100 mM glucose, 1 mM NADP$^+$, 1 U/ml GDH, 1 mM additive, 100 mM KPi, pH 8.0, total volume 20 ml; 1 hour; 20° C. The P450-BM3 concentration depended on the compound used 2: 1 µM, 3: 2.9 µM, 4: 2.9 µM, 5: 1.1 µM, 6: 2.7 µM)

| Alkane | Additive | Total product formed (mM) | TON | Regioselectivity |
|---|---|---|---|---|
| 2 | None | 0.15 | 150 | 2-:3-:4-Octanol = 12:44:44 |
| 2 | 1c | 1.16 | 1184 | 2-:3-:4-Octanol = 10:42:48 |
| 3 | None | 0.43 | 149 | 2-:3-Hexanol = 83:17 |
| 3 | 1e | 1.50 | 525 | 2-:3-Hexanol = 77:23 |
| 4 | None | 0.36 | 126 | 2-Hydroxy-3-methyl-:3-Hydroxy-3-methylpentane = 89:11 |
| 4 | 1c | 1.36 | 476 | 2-Hydroxy-3-methyl-:3-Hydroxy-3-methylpentane = 88:12 |
| 5 | None | 0.12 | 111 | only 2-Hydroxy-3,3-dimethylbutane |
| 5 | 1c | 0.96 | 892 | only 2-Hydroxy-3,3-dimethylbutane |
| 6 | None | 0.02 | 20 | only 2-Hydroxy-2,3-dimethylbutane |
| 6 | 1e | 0.19 | 3241 | only 2-Hydroxy-2,3-dimethylbutane |

The data show that the additives significantly increase the enzyme activity and also influence the regioselectivity.

The turnover numbers (TON) were calculated (mol of product/mol of enzyme) for the enzyme at the end of the reaction. These analyses show that both the regioselectivity and the activity of the enzyme can be influenced by the use of additives.

EXAMPLE 8

Chiral Analysis of n-hexane Hydroxylation Products

For the chiral analysis of 2- and 3-hexanol, the following instruments were used under the following conditions: AT 6890N (HP Agilent, USA); column: 15 m BGB-177/BGB-15 phase, internal diameter 0.25 mm, film thickness 0.25 µm, (BGB Analytik AG, Germany); pressure: 0.5 bar H$_2$; split rate 25; injector: 220° C.; temperature gradient: 40-200° C. at 0.5° C./min, FID detector. In both cases, for 2-hexanol and 3-hexanol, a change in the enantioselectivity was observed. In the case of 2-hexanol, a 25% increase in the enantiomeric excess for R-2-hexanol to ee$_R$ 43.9 was observed. In the case of 3-hexanol, the enantioselectivity was even reversed. This proves that the additives also influence the stereoselectivity of the CYP-catalysed reaction.

EXAMPLE 9

Hydroxylation of Gaseous Alkanes, e.g. $C_1$, $C_3$ and $C_4$ Alkanes

The hydroxylation of gaseous alkanes was carried out in a self-constructed low-pressure reactor. Twelve reaction vessels each having a total volume of 7 ml were filled with 2.5 ml of reaction mixture consisting of: 0.1 M D-glucose (Riedel de Haen), 1 mM NADP$^+$ (Codexis), 1 U/ml GDH (Codexis), 1 mM additive, BM3-WT enzyme (for the reaction of n-butane: 2.3 µM, propane: 2.9 µM, methane 1.3 µM) and 100 mM KPi, pH 8.0. Subsequently the reaction vessels were linked to a gas bottle via a multichannel gas feed. The following gas mixtures were used to flush the apparatus and to apply a pressure of 10 bar to the reaction solution: a) 7% methane, 8% oxygen, 85% nitrogen, b) 7% propane, 8% oxygen, 85% nitrogen or c) 10% butane, 8% oxygen, 82% nitrogen. The reaction mixture was stirred at 100 rpm with a crosshead-shaped magnetic stirrer (VWR). At the end of the reaction the pressure was carefully released from the reaction vessels, a 1 ml aliquot was centrifuged for 10 min at 13 000 rpm and analyzed by HPLC. A further aliquot of 1 ml volume was acidified with 0.1 ml of 10% HCl for later analysis by GC. Each experiment comprised at least one positive control for the enzyme activity, in which dodecanoic acid was added as additive (1 mM final concentration, from a 100 mM stock in DMSO), while the enzyme was exposed to 10 bar of the gaseous alkane mixture. The reaction of dodecanoic acid was analyzed using decanoic acid (1 mM final concentration, from a 100 mM stock in DMSO) as standard. The samples were extracted for the GC analysis with 0.5 volume of MTBE and were analyzed by GC.

EXAMPLE 10

GC Analysis of Butanol and Propanol

Butanol was analyzed by GC using the following instruments and under the following conditions: HP6890plus+ 7683HP (Hewlett Packard, USA); column: 15 m Stabilwax phase, internal diameter 0.25 mm, film thickness 0.5 µm, (J&W, Germany); pressure: 0.8 bar H$_2$; split rate 60; injector: 220° C.; temperature gradient: 40° C. 4 min isotherm, 40-60° C. at 4° C./min, 60-250° C. at 15° C./min. FID detector.

Propanol was analyzed by GC using the following instruments and under the following conditions: HP6890plus+ 7683HP; 530 (Hewlett Packard, USA); column: 15 m Free Fatty Acid Phase (FFAP) G/366; pressure: 0.5 bar H$_2$; sample volume 1 µl; injector: 220° C.; temperature gradient: 80-240° C. at 8° C./min, 250° C. for 15 min isotherm, FID detector.

EXAMPLE 11

GC Analyses of Methanol, Propanol and Butanol

For the GC-MS detection of butanol the following instruments were used under the following conditions: SSQ 7000

GC/MS system (Thermo Finnigan, USA); column: 15 m DB-Wax phase, internal diameter 0.25 mm, film thickness 0.5 μm, (J&W, Germany); pressure: 0.5 bar He; split rate 50; injector: 220° C.; temperature gradient: 30-60° C. at 4° C./min, 60-250° C. at 20° C./min.

For the GC-MS detection of propanol the following instruments were used under the following conditions: GC:HP6890+MS: HP5973 (Hewlett Packard, USA); column: 15 m DB-Waxetr phase, internal diameter 0.25 mm, film thickness 0.25 μm, J&W, Germany; pressure: 0.5 bar He; split rate 10; injector: 220° C.; temperature gradient: 40° C. 10 min, 40-240° C. at 16° C./min.

For the GC-MS detection of methanol the following instruments were used under the following conditions: GC: HP6890+MS: 5973 (Hewlett Packard, USA); column: 60 m Stabilwax phase, internal diameter 0.25 mm, film thickness 0.5 μm (Restek, Germany); pressure: 1.4 bar He; split rate 5; injector: 220° C.; temperature gradient: 60° C. 30 min isotherm, 60-240° C. at 16° C./min, 240° C. for 5 min isotherm.

EXAMPLE 12

HPLC Analyses of Methanol, Propanol and Butanol

The HPLC analyses were carried out using an LC-10A system, which was controlled by the LC-Solution Software (Shimadzu Deutschland GmbH, Duisburg, Germany). The modular built LC-System was equipped with LC-10AD pumps, an SIL-10A autoinjector, a CTO-10AC column oven, a differential refractive index detector RID-10A (all from Shimadzu Deutschland, Duisburg, Germany) or an electrochemical detector ED 50 (Dionex).

The separations were carried out using organic acid resin columns (300 mm length, 8 mm internal diameter and a pre-column of 40 mm length, 8 mm internal diameter; CS Chromatographie Service GmbH, Langerwehe, Germany) and 10 mM trifluoroacetic acid in water. The separations were carried out at 333 K at an elution rate of 1.0 ml/min.

The quantification of propanol and butanol was carried out using the RID-10A detector, while the quantification of methanol was carried out using the RID-10A or, preferably, the ED 50 detector. The ED 50 detector was operated in integrated, amperometric detection mode with an Ag reference electrode in the range of 300 nC. The detection was carried out in waveform as follows:

| Step | Time (sec) | Potential (V) | |
|---|---|---|---|
| 0 | 0.0 | +0.4 | |
| 1 | 0.28 | +0.4 | Begin |
| 2 | 0.30 | +0.4 | End |
| 3 | 0.31 | +0.4 | |
| 4 | 0.32 | +1.4 | |
| 5 | 0.44 | +1.4 | |
| 6 | 0.45 | −0.4 | |
| 7 | 0.88 | −0.4 | |

EXAMPLE 13

P450 BM3 Catalysed Oxidation of Butane and Propane

The P450 BM3 catalysed oxidation of butane and propane was carried out in the presence or absence of additives 1 under standard conditions as follows: 2.5 ml reaction volume, 5 ml gas volume, 1% DMF, 100 mM KPi, pH 8.0, 10 bar pressure (10% n-butane, 8% $O_2$, 82% $N_2$; 7% propane, 8% $O_2$, 85% $N_2$), propane oxidation: 14.5 h, butane oxidation: 17.5 h., 25° C. The results are shown in Table 2.

| Alkane | Additive | Total product formed (mM) | TON | % ee |
|---|---|---|---|---|
| Butane | None | 1.2 | 527 | 24 |
| Butane | 1a | 1.1 | 469 | 32 |
| Butane | 1b | 8.4 | 3632 | 22 |
| Butane | 1c | 2.0 | 879 | 23 |
| Butane | 1d | 3.9 | 1699 | 20 |
| Butane | 1e | 5.8 | 2519 | 19 |
| Propane | 1e | 3.0 | 1021 | — |
| Propane | 1f | 0.67 | 227 | — |
| Propane | 1h | 0.50 | 170 | — |

As previously, the presence of additives results in an increase of the enzyme activity and an increase in product formation. In both cases only traces, if any, of 1-butanol and 1-propanol were detected (~1%).

EXAMPLE 14

P450 BM3 Catalysed Oxidation of Methane

The P450 BM3 catalysed oxidation of methane was carried out in the presence of an additive 1 with formation of methanol as follows: 2.5 ml reaction volume, 5 ml gas volume, 1 mM additive, 100 mM KPi, pH 8.0, 10 bar pressure (7% methane, 8% $O_2$, 85% $N_2$), 21 h., 25° C. The results are shown in Table 3.

| Additive | Total product formed (mM) | TON |
|---|---|---|
| 1c | 2.75 | 2053 |
| 1d | 3.31 | 2472 |
| 1e | 1.81 | 1353 |
| 1f | 1.25 | 933 |
| 1g | 0.75 | 560 |
| 1h | 0.28 | 210 |

Without additive, no notable conversion of methane occurred. In contrast, the addition of additives led to considerable conversion of methane to methanol.

EXAMPLE 15

P450 BM3 Catalysed Oxidation of Methane

The P450 BM3 catalysed oxidation of methane was carried out in the presence of an additive with formation of methanol as follows: 2.5 ml reaction volume, 5 ml gas volume, 1 mM additive, 100 mM KPi, pH 8.0, 10 bar pressure (7% methane, 8% $O_2$, 85% $N_2$), 19 h., 25° C. The results are shown in Table 4.

| Additive | Total Product formed (mM) | TON |
|---|---|---|
| 1H, 1H, 2H, 2H-perfluorooctan-1-ol | 2.53 | 1889 |
| 1H, 1H, 2H, 2H, 3H, 3H-Perfluoroundecano | 0.84 | 630 |
| 6(perfluoroethyl) hexanol | 2.69 | 2006 |

As in the previous example, no notable conversion of methane occurred without additive. In contrast, the use of partially fluorinated alcohols led to a considerable formation of methanol. In the case of methane and propane, in which no notable conversions are observed without additive, the presence of the additive leads to substrate acceptance. The additives are thus suitable not only for increasing the enzyme activity and manipulation of the regio- and stereo-selectivity, but also for changing the substrate acceptance. The additives probably position the substrates, previously not located at the heme, at the right distance from the iron atom and thus enable their conversion. In some cases, the additives, by reducing the volume of the active site, could increase the substrate concentration at the heme and thus the probability of their conversion.

The invention claimed is:

1. A method for oxidizing an organic alkane compound in the presence of a perfluorinated organic compound, said method comprising:
   (i) providing a reaction mixture comprising, in an aqueous solution:
      (a) an alkane compound selected from the group consisting of a C1-C8 alkane,
      (b) a cytochrome P450 enzyme (CYP), and
      (c) a perfluorinated organic compound in an amount sufficient to activate oxidation of the alkane by the CYP; and
   (ii) reacting in the provided reaction mixture said alkane compound with said CYP, for a period of time and conditions sufficient to oxidize the alkane compound, thereby obtaining the oxidized organic compound.

2. The method as claimed in claim 1, wherein the perfluorinated organic compound is selected from the group consisting of perfluorinated alkanes having the general formula (I)

$$CF_3(CF_2)_nCF_3 \tag{I}$$

where n=3 to 30, and perfluorinated aromatic compounds having optionally at least one functional group.

3. The method as claimed in claim 2, wherein the functional group is selected from the group consisting of —OH —COOH, —SO$_3$H and/or —PO$_3$H or salts thereof.

4. The method as claimed in claim 3, wherein the counterion of the salt is selected from the group consisting of Li$^+$, Na$^+$, K$^+$, Cs$^+$, Mg$^{+2}$, Zn$^{+2}$, H$_4$N$^+$ or (n-butyl)$_4$N$^+$.

5. The method as claimed in claim 1, wherein the perfluorinated organic compound is selected from the group consisting of perfluorinated carboxylic acids having the general formula (II):

$$CF_3(CF_2)_nCO_2H \tag{II}$$

where n=0 to n=30, pentafluorobenzoic acid or salts thereof.

6. The method as claimed in claim 1, wherein the perfluorinated organic compound is perfluoro-n-octanol.

7. The method as claimed in claim 1, wherein the reaction mixture further comprises an oxidizing agent, selected from the group consisting of atmospheric oxygen, H$_2$O$_2$, cumene hydroperoxide, tert-butyl hydroperoxide, linoleic acid hydroperoxide, NaClO$_2$ and/or NaIO$_4$.

8. The method as claimed in claim 1, wherein the aqueous solution further comprises an ionic solvent or an organic solvent as a co-solvent.

9. The method as claimed in claim 8, wherein the co-solvent comprises supercritical CO$_2$, dimethylformamide, acetonitrile, or tetrahydrofuran.

10. The method as claimed in claim 1, wherein said provided CYP (b) is provided in the aqueous solution as isolated enzymes or as CYP-expressing whole cells.

11. The method as claimed in claim 1, wherein the cytochrome is selected from bacterial CYPs of the CYPs 102 class.

12. The method as claimed in claim 11, wherein the bacterial CYPs of the CYPs 102 class is selected from the group consisting of CYP102A1, CYP102A2, CYP102A3, CYP102A4, CYP102A5, CYP102A6, CYP102A7, CYP102A8, CYP102A9, CYP102A10, CYP102A11, and CYP102A12.

13. The method as claimed in claim 1, wherein the cytochrome P450 used is the cytochrome enzyme P450 BM3.

14. The method as claimed in claim 1, wherein the oxidized organic compound is an alcohol.

* * * * *